United States Patent [19]

Plumb

[11] Patent Number: 4,919,892

[45] Date of Patent: * Apr. 24, 1990

[54] APPARATUS FOR DETECTING OIL AND OTHER LIGHTER-THAN-WATER CONTAMINANTS IN AN EFFLUENT STREAM

[76] Inventor: Arnold D. Plumb, P.O. Box 35646, Tulsa, Okla. 74153

[ * ] Notice: The portion of the term of this patent subsequent to Sep. 5, 2006 has been disclaimed.

[21] Appl. No.: 369,770

[22] Filed: Jun. 22, 1989

Related U.S. Application Data

[63] Continuation-in-part of Ser. No. 203,416, Jun. 7, 1988, Pat. No. 4,863,692.

[51] Int. Cl.⁵ .............................................. G01N 33/28
[52] U.S. Cl. .......................................... 422/58; 422/61; 422/87; 422/88; 436/1; 436/3; 436/28; 436/29; 436/61; 436/163; 73/61.1 R; 73/323; 73/863.71; 73/863.82; 210/93; 210/95; 210/671; 166/336; 166/337
[58] Field of Search ............... 422/58, 61, 86–88; 436/1, 3, 28, 29, 60, 61, 163; 73/61 R, 61.1 R, 323, 863.71, 863.81, 863.82; 210/93, 94, 95, 671; 166/336, 337

[56] References Cited

U.S. PATENT DOCUMENTS

| | | |
|---|---|---|
| 3,192,764 | 7/1965 | Jasek .................... 73/61.1 R |
| 3,400,575 | 9/1968 | Madden ...................... 73/61 R |
| 3,845,661 | 11/1974 | Hollweck et al. ................ 374/208 |
| 3,887,907 | 6/1975 | Brill ............................ 73/863.21 X |
| 3,924,449 | 12/1975 | Moreau et al. .................. 73/61.1 R |
| 3,929,003 | 12/1975 | Llewellyn ........................ 73/61.1 R |
| 3,985,020 | 10/1976 | Moreau ............................ 73/61.1 R |
| 4,131,773 | 12/1978 | Maham et al. ................... 200/61.05 |
| 4,223,552 | 9/1980 | Goldstein ........................ 73/61.1 R |
| 4,287,763 | 9/1981 | Richard ............................ 73/863.21 |
| 4,303,408 | 12/1981 | Kim et al. ............................ 436/175 |
| 4,363,639 | 12/1982 | Gladon ................................. 55/95 |
| 4,511,461 | 4/1985 | Kruyer ................................. 209/47 |
| 4,658,861 | 4/1987 | Roberson, Sr. ....................... 138/90 |
| 4,863,692 | 9/1989 | Plumb ............................... 422/58 |

Primary Examiner—Barry S. Richman
Assistant Examiner—Lynn M. Kummert
Attorney, Agent, or Firm—Pavel, Gambrell, Hewitt, Kimball & Krieger

[57] ABSTRACT

An apparatus for detecting oil and other lighter-than-water contaminants in an effluent stream in a sewage system. The apparatus includes a disposable detector which floats in the effluent stream and detects oil and other contaminants having a specific gravity lighter than the water by absorbing the oil and such contaminants in an oleophilic material, permitting the oil and other contaminants to rise and collect in a collection tube. The acidity of pH of the effluent being monitored is determined by routing a portion of the effluent stream across a litmus paper.

15 Claims, 2 Drawing Sheets

APPARATUS FOR DETECTING OIL AND OTHER LIGHTER-THAN-WATER CONTAMINANTS IN AN EFFLUENT STREAM

RELATED APPLICATION

This is a continuation-in-part application of Ser. No. 203,416 filed June 7, 1988, now U.S. Pat. No. 4,863,692.

BACKGROUND OF THE INVENTION

1. Field of the Invention

This invention relates to an apparatus for detecting oil and other lighter-than-water contaminants in an effluent stream, and in one of its aspects, this invention relates to an apparatus for continuously detecting the presence of oil and other lighter-than-water contaminants and the acidity or pH of an effluent stream.

2. Description of the Prior Art

Environmental regulations have been promulgated which require that the effluent stream of commercial establishments be monitored to determine if any oil is being discharged and to measure the pH of the waste water.

Consequently, there is a need for an inexpensive and disposable detector which can be inserted into the sewage system of a commercial or other establishment using the conventional access line. While there are apparatus for detecting the presence of oil in a body of water (for example U.S. Pat. Nos. 4,131,773 and 4,223,552) and for extracting a sample from a stream at a specified time (for example U.S. Pat. No. 3,400,575), there is a need for a device which can be installed directly into a sewage system to continuously sample the effluent stream.

SUMMARY OF THE INVENTION

Briefly, the invention relates to an apparatus for detecting oil and other lighter-than-water contaminants in an effluent stream. The detector, which is secured within the pipeline, includes a housing having an inlet and an outlet. Supported within the housing is an oleophilic material through which at least a portion of the effluent stream passes. A series of baffles confine the oleophilic material and serve to create a zone in which separation occurs of the oil and other contaminants from the water in a sampled portion of the effluent.

Oil and other contaminants having a specific gravity lighter than water are absorbed by the oleophilic material and migrate upwardly to the top of the oleophilic material. At that point, the oil and other contaminants are routed through a channel zone into a collection tube for visual observation when the detector is removed. A portion of the effluent stream passes through a second zone where the pH of the effluent stream is measured. The baffles also serve to channel the oil and other contaminants to the collection tube and they also route the remaining portion of the effluent stream through the second zone and eventually through the outlet of the housing.

Examples of the more important features of this invention have been summarized rather broadly in order that the detailed description may be better understood. There are, of course, additional features of the invention which will be described hereafter and which will also form the subject of the claims appended hereto.

BRIEF DESCRIPTION OF THE DRAWINGS

In order to more fully understand the drawings used and the detail description of the present invention, a brief description of each drawing is provided.

DETAILED DESCRIPTION OF THE PREFERRED EMBODIMENT

Figure 1:
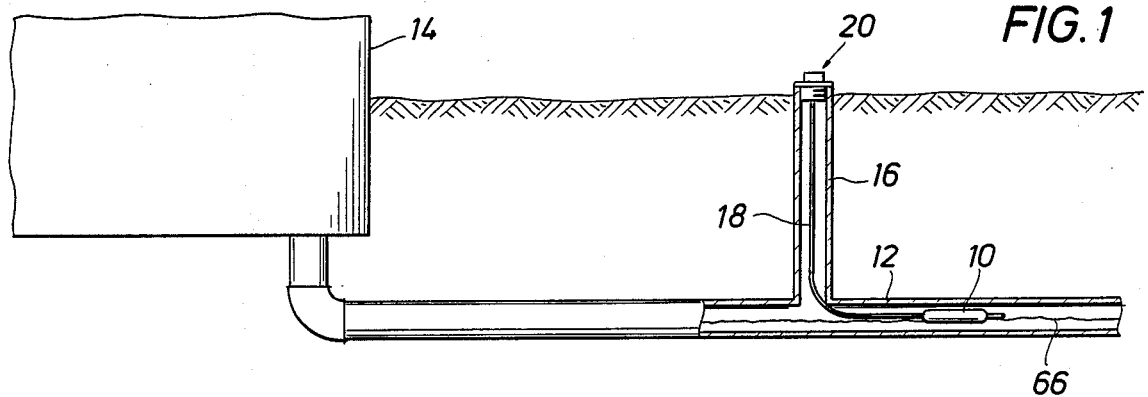
FIG. 1 is a cross-sectional elevation view illustrating the present invention installed in a sewage system.

Referring to FIG. 1, a detector 10 is secured within the sewage system 12 of a building structure 14. The sewage system includes an access line 16 through which the detector 10 is inserted and retrieved. The detector is held in place by a line 18 which is secured near the top of the access line by a securing system 20. The detector 10 floats in an effluent stream 66.

Referring now to FIGS. 2-6, the detector comprises a housing 22 having an inlet such as apertures 24 and an outlet 26. An oleophilic material 28 is supported within the housing 22. As shown in FIG. 1, the housing includes a baffle 30 proximate the apertures 24 and a baffle 32 proximate the outlet 26. Preferably, baffles 30 and 32 are of equal height and extend slightly above the centerline of housing 22.

A baffle 34 extends from the rear portion of the housing 22 upwardly toward the interior of the top of the housing 22. The baffle 34 includes a front portion 35 which extends downwardly in front of baffle 32 to a point below the top portion of baffles 30 and 32.

In this manner, the housing 22 is divided up into three zones. A first zone 36 which occupies the front portion of the housing between the apertures 24 and the baffle 30; a second zone 38 within which the oleophilic material 28 is supported and which includes that portion of the housing between the baffles 32 and 34 extending to the outlet 26; and a third zone 40 at the rear of the housing between the interior surface of the housing and the baffle 34. The rear of the housing 22 includes an aperture 42 to which a collection tube 48 is attached or integrally formed therewith.

The front portion of the housing 22 includes a nozzle member 62 onto which line 18 is secured. The nozzle member 62 may include a series of burrs or upsets 63 to anchor line 18 to the detector 10.

Figure 3:
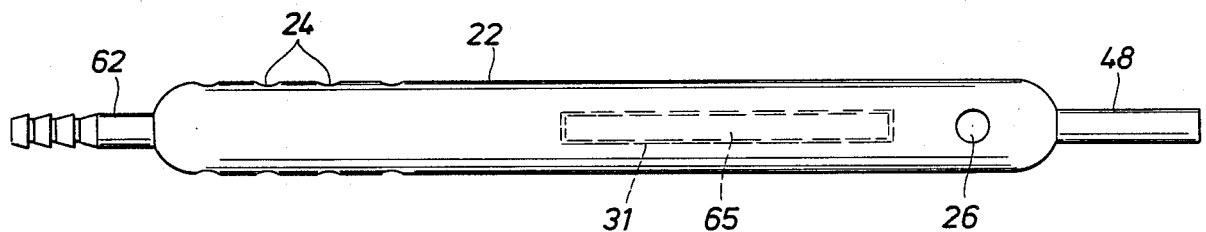
FIG. 3 is a bottom view of the detector partially in section.
Figure 4:
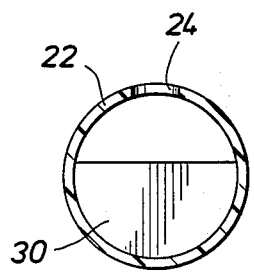
FIG. 4 is a cross-sectional view taken along line 4—4 of FIG. 2.
Figure 5:
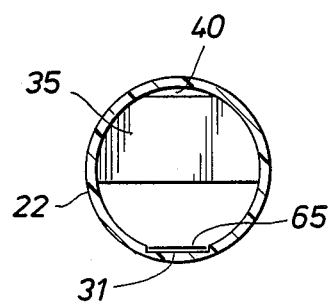
FIG. 5 is a cross-sectional view taken along line 5—5 of FIG. 2.
Figure 6:
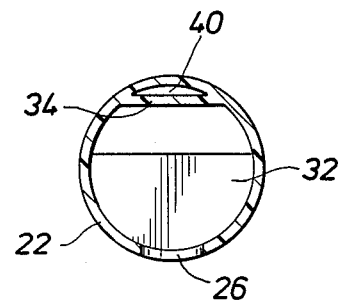
FIG. 6 is a cross-sectional view taken along line 6—6 of FIG. 2.

Referring now to FIG. 3, a strip of litmus paper 65 is situated at the bottom of zone 38 and held in place by the oleophilic material 28. Alternatively, the housing 22 may be molded with an inset channel region 31 to secure a predetermined size of litmus paper.

Figure 7:
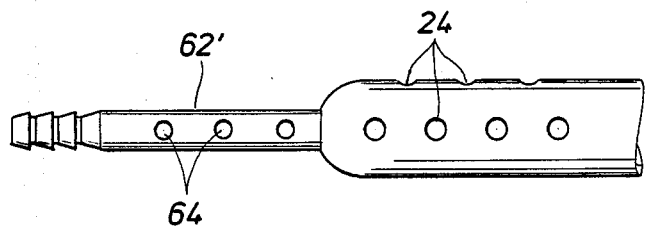
FIG. 7 is an alternate embodiment of the intake portion of the detector.

With particular reference to FIG. 7, an alternative embodiment of the front portion of the detector 10 is shown. The nozzle member 62' includes a plurality of apertures 64 along at least a portion of the length of its circumference. As shown, the inlet for passage of at least a portion of the effluent stream 66 into the detector comprises apertures 24 and 64. Based on the amount of fluid communication desirable, use of only apertures 64 may be sufficient. The member 62' may be an elongated tube which extends upwardly and eventually connects with line 18.

In the operation of the apparatus, a detector 10 is placed within the sewage system 12 so that the housing 22 floats on the surface of the effluent stream 66. In this manner, at least a portion of the effluent stream enters through apertures 24. The effluent contacts baffle 30 which only permits a portion of the effluent which rises above the level of the baffle 30 to pass over it to the oleophilic material 28. The oleophilic material attracts oil within the effluent stream and the oil migrates upwardly since it is lighter than the remaining portion of the effluent stream. Since the vertical portion 35 of baffle 34 extends below the top of baffles 30 and 32, oil and other contaminants which rise within the oleophilic material will not be rejected through outlet 26 but rise to the top of zone 38 and then migrate rearwardly toward zone 40. Eventually, the trapped oil and other contaminants passes through zone 40 and aperture 42 into collection tube 48. Collection tube 48 includes a small pin hole 66 which permits the evacuation of air and thereby permits the captured oil to completely fill zone 40 and collection tube 48.

Since the vertical portion of baffle 34 extends below the top of baffles 30 and 32, the vertical migration of the oil and other contaminants within zone 38 is enhanced while the heavier fluid is permitted to remain or alternatively rise over baffle 32 and pass out through outlet 26. The baffle 30 also serves to prevent the effluent stream captured within zone 38 from running back out through the apertures 24.

The effluent stream which passes over baffle 30 and enters zone 38 will contact the litmus paper 64 located below the oleophilic material. In this manner, the pH is measured.

Preferably, the housing 22 is made of a polyvinylchloride clear plastic tubing as is the collection tube 48. Since they are clear, the oil in the collection tube and the pH measured by the litmus paper are easily observable. Preferably, the housing 22, baffles 30, 32 and 34, and collection tube 48 are manufactured as an integral unit or the detector may be manufactured in discrete portions, such as longitudinal halves, and then ultrasonically welded.

The oleophilic material may be made of polyurethane material as manufactured by such companies as Polyurethane Products of Addison, Ill., and Plastics Specialities of Austin, Tex. These materials are characterized occasionally as "sorbents." The litmus paper used may be any commercially available paper such as the type Color Phust ® manufactured by MCB Incorporated of Gibbstown, New Jersey. The litmus paper may include various levels of sensitivity and may measure the full range of pH desirable (i.e., acidic or alkaline).

Preferably, the cross-sectional area of the outlet 26 is smaller than the sum of the cross-sectional area of the apertures 24 to create a pressure differential and restrict the flow of the effluent stream passing through the support member. In this manner, the entrapment of oil contaminants within the oleophilic material is promoted. The cross-sectional area of the outlet 26 should not be more than 70 percent of the sum of the cross-sectional areas of the apertures 24 to achieve optimum results.

Based on experimentation, it has been determined that for an effluent stream having one part oil to four parts water, there will be a visible collection of oil in the collection tube 48 within five minutes of immersion in the effluent stream. In these particular experiments, the oleophilic material used was Scot Foam ®, which is available through Scot Foam, a division of GFI of Eddystone, Pennsylvania.

While the detector may be inserted in the sewage system and left there for an extended period of time, it may also be installed and left in place for only a few moments to obtain a current reading.

Figure 8:
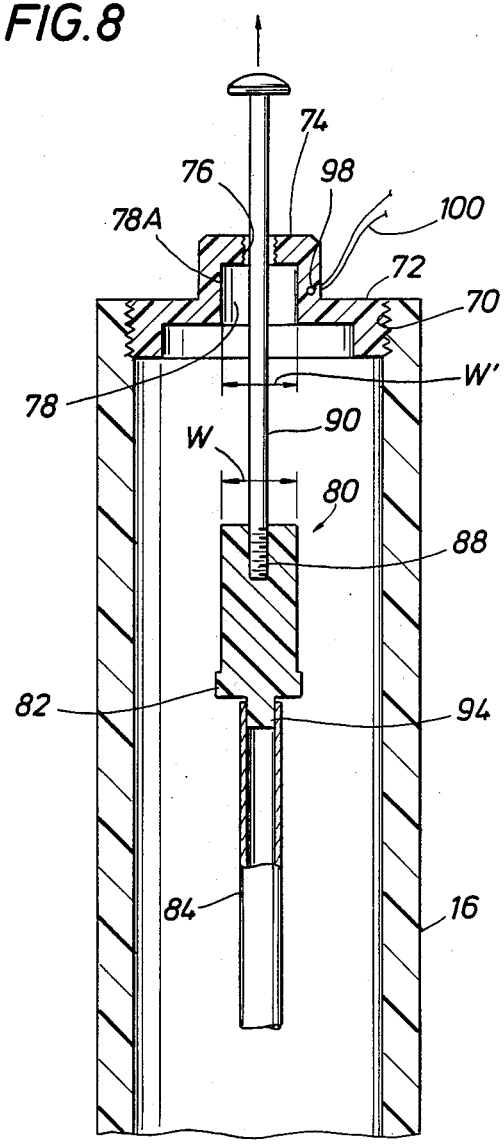
FIG. 8 is a cross-sectional elevation view of a portion of a securing system for attaching the detector to the access line.
Figure 9:
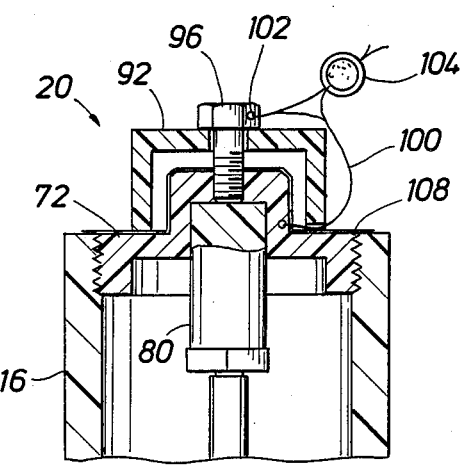
FIG. 9 is a cross-sectional elevation view of the securing system shown in a final position.

Reference is now made to FIG. 8 for a discussion of the attachment of the detector 10 to the access line 16. In typical commercial establishments the access line 16 includes a threaded portion 70 adapted to receive a cap 72. Therefore, the present invention is intended to accommodate the use of existing access lines 16. The cap 72 includes a raised portion 74 to permit the use of a wrench or other tool to tighten the cap 72 to the access line 16 once threadably engaged. The raised portion 74 includes a threaded section 76, the purpose of which is discussed below. Within the raised portion 74 is a recessed portion or area 78. The recessed area 78 is adapted to receive a plug member 80. The plug member 80 includes a connector portion 82 which is attached to the lead line 18. The plug also includes a threaded portion 88 to receive a key 90 whose operation is described below. The dimension W of the plug 80 is selected to fit in a snug manner within the dimension W' of the recessed area 78. Since the cap 72 and plug 80 would be made of polyvinylchloride (PVC) typically, the dimensions W and W' may be substantially the same. Alternatively, the wall 78A of the recessed portion may be tapered inwardly slightly as shown to provide a snug fit. A cover 92 is adapted to be inserted over the raised portion 74 of the cap 72 and attached by means of a bolt 96 or other threaded member to the threaded portion of the cap.

Figure 2:
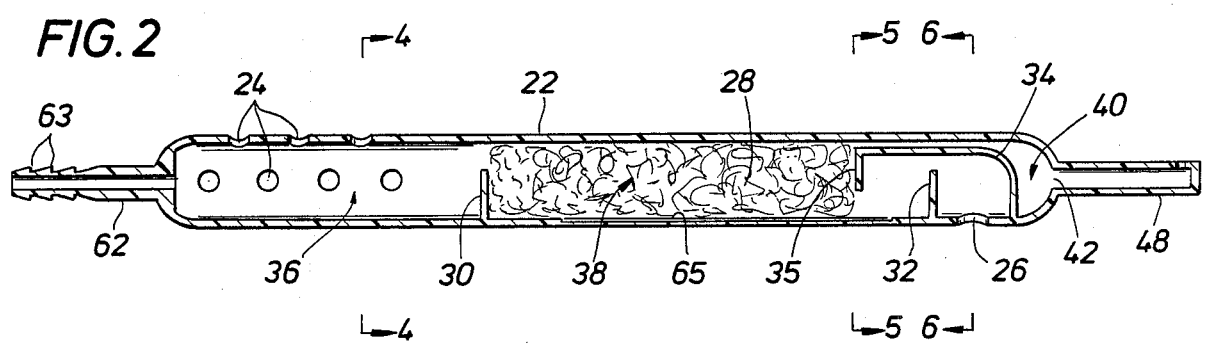
FIG. 2 is a cross-sectional elevation view of the detector portion of the present invention.

In the operation of this portion of the invention, the lead line 18, which is already attached to the detector 10 at one end, is attached at its other end to the connector 82. The connection may be made by a nipple 94 which is inserted into the inlet member or lead line. The detector is then inserted down the access line 16 into the main sewage line taking into account the radius or bend of the lead line 18 so that the detector is oriented properly as shown in FIG. 2 with the collection tube at the top. The key 90 is then passed through the threaded portion 76 of the cap 72 and threadably engaged with the threaded portion 88 in the plug 80. Since the threaded portion 76 has a larger diameter than the outer diameter of the key 90, the key 90 will slide easily within threaded portion 76. The cap 72 is then screwed into the threaded portion of the access line 16. And since the key 90 can slide within the threaded portion 76, the cap 72 may be screwed down onto the access line without rotating the key 90 and thereby twisting the detector within the sewage system. The plug 80 is then pulled into the recessed area 78 by pulling up on the key 90, and the plug is thereby held in place by a friction connection. At that point, the key 90 may be easily unscrewed from the threaded portion 88 of the plug because of the friction fit of the plug 80 within the cap 72. The cover 92 is then placed over the cap 72 and a bolt 96 fastens the cover 92 to the cap 72. The bolt 96 also seals against the top of the cover 92 thereby prohibiting seepage of offensive sewage odors out of the access line.

To record if anyone tampers with the detector, the raised portion 74 of the cap includes an aperture 98 and a wire 100 is passed through the aperture 98 and a passageway 102 within the head of the bolt 96. A security lock or lead crimp 104 may then be inserted and crimped sealed. Such security locks are of a style Lead Seal ® manufactured by E.J. Bruks of Dallas, Tex. As a back up or alternative security measure to ensure that no one has tampered with the detector, an adhesive tape 108 may be stretched across the top of the access line and the cap. The tape would include a hole for the bolt 96 to pass through or one may be made easily by the installer. After the tape is placed, the cover 92 would be installed. The tape 108 as well as the lead crimp lock 104 may include written materials and other descriptors of the appropriate regulatory authority, the date of inspection, the type of detector, etc. Thus, if anyone tried to remove the cap the lead crimp 104 would be damaged which would indicate a tampering. Further, if anyone tried to remove the cover, the tape would reflect such.

Figure 10:
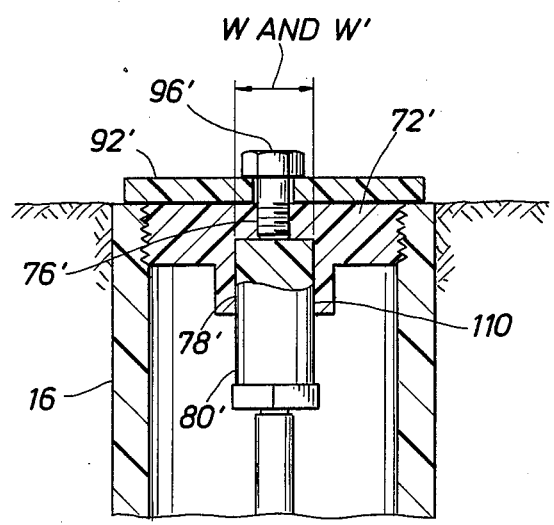
FIG. 10 is an alternate embodiment of the securing system shown in FIG. 8.

Referring now to FIG. 10, an alternate embodiment of the cap 72' and cover 92' is shown. The plug 80' is similar to that disclosed previously with respect to FIG. 7. The cap 72' is flat to permit vehicles to pass over or to provide a flush contour at the ground surface for whatever reason. The cap 72' includes a recess portion 78' defined by walls 110. Again, the dimension W' is selected so that it is substantially the same as the dimension of W of the plug or tapered to provide a snug fit as described above. The cap 72' includes a threaded portion 76' to receive a bolt 96' which is used to secure the cover 92' to the top surface of the cap 72' once the plug 80' is installed. The operation of the alternate embodiment shown in FIG. 10 is identical to that discussed earlier with respect to FIG. 8. That is, the detector is installed in the access line 16 in the manner described above and a key 90 is then passed through the cap 72' and attached to the plug. The cap 72' is then screwed down flush with the ground surface and the key is pulled upwardly engaging the plug within the recessed area 78' of the cap 72'. The key 90 is then unscrewed, the cover 92' installed, and the bolt 96' inserted. To ensure that no one tampers with the detector, a tape may be passed across the top of the access line and the cap before the cover is installed as discussed earlier. The unit may be sealed with a wax or resin with the seal of the public agency impressed within the seal or resin thereby permitting the sealing of the system without the worry of vehicles destroying the verification system.

Obviously, the embodiment shown in FIG. 10 may be easily modified based on this disclosure to make it more flush with the ground surface. For example, the top of the access line 16 and the cap 72' may include a recessed area which would permit the cover 92' to be flush with the ground surface once installed. The region for the bolt head 96' within the cover 92' would then be countersunk so that the top of the bolt would be flush with the top of the cover 92' as well as the ground surface.

In removing the detector for inspection, the inspector would merely break the seals and disassemble the cap. That is, the bolt 96 would be unscrewed and the cover 92 removed. At that time, the key 90 would be inserted through the threaded portion 76 and screwed into the threaded portion 88 of the plug 80. The key would then be pushed downwardly thereby dislodging the plug from the cap. Since the key includes a head, it may be released and would still hang from the top of the cap 72 holding the plug 80 and detector 10. The cap 72 would be unscrewed from the access line 16 and the entire assembly removed. Since the detector is attached by means of the lead line to the plug, the entire assembly is easily removed. A quick visual inspection of the collection tube 48 as well as the litmus paper 64 will give the inspector an indication of whether or not oil has been dispersed in the effluent stream and the maximum or minimum pH of the effluent stream since the last inspection. If the inspector wishes to obtain an immediate sampling, a new indicator may be installed and sampling obtained over a short period of time. Since the detectors are disposable, there is no need to disassemble each detector for cleaning before it is used.

The present invention has been described in terms of particular embodiments. Obviously, modifications and alterations to these embodiments will be apparent to those skilled in the art in view of this disclosure. It is, therefore, intended that all such equivalent modifications and variations fall within the spirit and scope of the present invention as claimed.

What is claimed:

1. An apparatus for continuously detecting the presence of oil and other contaminants in an effluent stream passing through a pipeline comprising:
    a housing having an inlet and an outlet;
    oleophilic means supported within said housing and positioned so that at least a portion of the effluent stream enters said housing through said inlet and passes through said oleophilic means;
    means for directing the flow of the effluent stream within said housing; and
    a tube having one end in fluid communication with the interior of said housing and having another end substantially restricted, said tube positioned to collect and display the presence of oil absorbed by said oleophilic means.

2. The apparatus of claim 1 wherein said directing means comprises a plurality of baffles.

3. The apparatus according to claim 2 wherein said plurality of baffles comprises:
    a first baffle and a second baffle attached to said housing, said first and second baffles positioned and arranged to laterally support said oleophilic means; and
    a third baffle positioned and arranged to isolate oil and other contaminants separated from the effluent stream by said oleophilic means and to direct the oil and other contaminants to said tube.

4. The apparatus of claim 1 wherein said apparatus further comprises means for detecting the pH of the effluent stream.

5. The apparatus of claim 4 wherein said pH detecting means comprises litmus paper.

6. The apparatus of claim 1 wherein the cross-sectional area of said outlet is sized to be no more than 70% of the cross-sectional area of said inlet to form a pressure differential promoting the movement of the oil towards said tube.

7. The apparatus of claim 6 wherein said apparatus further comprises means for detecting the pH of the effluent stream.

8. The apparatus of claim 7 wherein said pH detecting means comprises litmus paper.

9. An apparatus for continuously detecting the presence of oil and other contaminants in an effluent stream passing through a pipeline comprising:
   a housing having an inlet and an outlet;
   oleophilic means supported within said housing and positioned so that at least a portion of the effluent stream enters said housing through said inlet and passes through said oleophilic means;
   means for supporting said oleophilic means within said housing and for directing the flow of the effluent stream through said oleophilic means so that oil and other contaminants absorbed by said oleophilic means are permitted to rise through said oleophilic means and the remainder of the effluent stream is directed through said outlet; and
   a tube in fluid communication with the interior of the housing for collecting and displaying the presence of oil and other contaminants rising through said oleophilic means.

10. The apparatus of claim 9 wherein said supporting and directing means comprises a plurality of baffles.

11. The apparatus according to claim 10 wherein said plurality of baffles comprises:
   a first baffle and a second baffle attached to said housing, said first and second baffles positioned and arranged to laterally support said oleophilic means; and
   a third baffle positioned and arranged to direct and isolate oil and other contaminants rising through said oleophilic means.

12. The apparatus of claim 7 wherein the cross-sectional area of said outlet is sized to be no more than 70% of the cross-sectional area of said inlet to form a pressure differential promoting the movement of the oil towards said tube.

13. The apparatus according to claim 7 wherein said apparatus further comprises means for securing said housing to said pipeline.

14. The apparatus according to claim 13 wherein said securing means comprises:
   a line member positioned and arranged to engage said housing proximate said inlet;
   a cap positioned and arranged to engage said pipeline and having a recessed portion of a predetermined minimum width;
   a plug having an exterior width substantially the same as said predetermined minimum width of said cap and a connector positioned and arranged to engage said line member;
   a cover positioned and arranged to contact said cap; and
   means for verifying the movement of the cap relative to the cover.

15. An apparatus for continuously detecting the presence of oil and other contaminants in an effluent stream passing through a pipeline comprising:
   a housing having an inlet and an outlet;
   oleophilic means supported within said housing and positioned so that at least a portion of the effluent stream enters said housing through said inlet and passes through said oleophilic means;
   means for supporting said oleophilic means within said housing and for directing the flow of the effluent stream through said oleophilic means so that oil and other contaminants absorbed by said oleophilic means are permitted to rise through said oleophilic means and the remainder of the effluent stream is directed through said outlet;
   a tube in fluid communication with the interior of the housing for collecting and displaying the presence of oil and other contaminants rising through said oleophilic means; and
   means for detecting the pH of the effluent stream.

* * * * *